United States Patent [19]

Stieber

[11] Patent Number: 5,606,134
[45] Date of Patent: Feb. 25, 1997

[54] SCORE BEND TESTING APPARATUS AND METHOD

[75] Inventor: Jeffrey M. Stieber, Green Bay, Wis.

[73] Assignee: Green Bay Packaging, Inc., Green Bay, Wis.

[21] Appl. No.: 492,785

[22] Filed: Jun. 21, 1995

[51] Int. Cl.⁶ .................................................. G01N 3/20
[52] U.S. Cl. ............................................. 73/849; 73/854
[58] Field of Search ............................ 73/760, 849, 854, 73/862.391, 862.454

[56] References Cited

U.S. PATENT DOCUMENTS

| | | | |
|---|---|---|---|
| 2,646,679 | 7/1953 | Buker | 73/854 |
| 3,178,936 | 4/1965 | Finsterwalder | 73/854 |
| 4,358,962 | 11/1982 | Ashby et al. | 73/849 |
| 5,022,273 | 6/1991 | Evans | 73/849 |
| 5,419,202 | 5/1995 | Howard et al. | 73/849 |

Primary Examiner—Richard Chilcot
Assistant Examiner—Max H. Noori
Attorney, Agent, or Firm—Andrus, Sceales, Starke & Sawall

[57] ABSTRACT

A score bend testing apparatus consists of a base having an upwardly facing support surface which supports a scored sheet of material. The support defines a forward edge, and the score is positioned forwardly of the forward edge while the rearward portion of the sheet is clamped against the support by a clamping device. A force gauge assembly is moved downwardly to engage the sheet of material forwardly of the score, and downward movement of the force gauge assembly results in the sheet of material being bent at the score. The force gauge assembly determines the amount of force required to bend the sheet of material. The force gauge assembly is mounted to a cross-member which extends between movable output members associated with rodless pneumatic cylinders.

17 Claims, 4 Drawing Sheets 5,606,134

SCORE BEND TESTING APPARATUS AND METHOD

BACKGROUND AND SUMMARY OF THE INVENTION

This invention relates to an apparatus and method for testing or determining the amount of force required to bend a sheet of material, such as corrugated board, along a score line.

In the manufacture of material such as corrugated board or paperboard, it is common to provide scores or other demarcations at locations where a blank is to be folded. Such scores or demarcations can provide varying degrees of ease of folding of the blank, and it is desirable to know the amount of force required to bend the blank at the score. This is especially the case when the bend or fold is to be made using automated equipment.

It is an object of the present invention to provide an apparatus and method for testing the amount of force required to bend a sheet of material such as corrugated board or paperboard along a score or other demarcation. It is a further object of the invention to provide an apparatus which is relatively simple in its construction and operation, yet which is capable of providing a high degree of accuracy in determining the amount of force required to bend the sheet of material at the score. Yet another object of the invention is to provide a method which is easily and simply carried out using a relatively small number of steps. A still further object of the invention is to provide a quick and easy score bend or folding test which can be quickly repeated by an operator in a safe and efficient manner.

In accordance with the invention, a score bend testing apparatus includes a base having an upwardly facing planar support surface defining a forward edge, and a clamp for clamping the sheet of material, such as corrugated board or paperboard, against the support surface such that the score is located outwardly or forwardly of the edge. A force applying arrangement applies a downward force to the sheet of material outwardly or forwardly of the score, and continues application of the downward force until the sheet of material bends at the score. A force measuring arrangement is interconnected with the force applying arrangement for determining the amount of force required to bend the sheet at the score. The upwardly facing planar surface of the base is oriented at an angle to horizontal, such that the portions of the base rearwardly of the forward edge slope downwardly. The base includes an upstanding member associated with its rear portion, which is adapted to engage a rear edge defined by the sheet of material to position the sheet of material relative to the forward edge of the base. The clamp is preferably mounted to the upstanding member, and includes an extendable and retractable member for selectively engaging the sheet of material to clamp it against the base. The force applying arrangement includes a pair of spaced supports located one on either side of the base, with the sheet of material being disposed between the spaced supports. An operating device, such as a pneumatic cylinder assembly, is mounted to each support. Each operating device includes an output member which is selectively movable in an upward and downward direction. A cross-member extends between and is interconnected with the output members for selective upward and downward movement therewith. An engagement member is mounted to the cross-member for engaging the sheet of material upon downward movement of the cross-member. The engagement member is preferably a rod-like member which extends along an axis parallel to the forward edge of the base and to the score. The cross-member is disposed forwardly of the base forward edge, and extends parallel relative thereto. The force measuring arrangement is mounted to the cross-member and, in a preferred embodiment, the force applying arrangement and force measuring arrangement are in the form of an integral force gauge unit secured to the cross-member.

The invention also contemplates a method of determining the amount of force required to bend a sheet of material at a longitudinal score, substantially in accordance with the foregoing summary.

Various other features, objects and advantages of the invention will be made apparent from the following description taken together with the drawings.

BRIEF DESCRIPTION OF THE DRAWINGS

The drawings illustrate the best mode presently contemplated of carrying out the invention.

In the drawings.

DETAILED DESCRIPTION OF THE INVENTION

Figure 1:
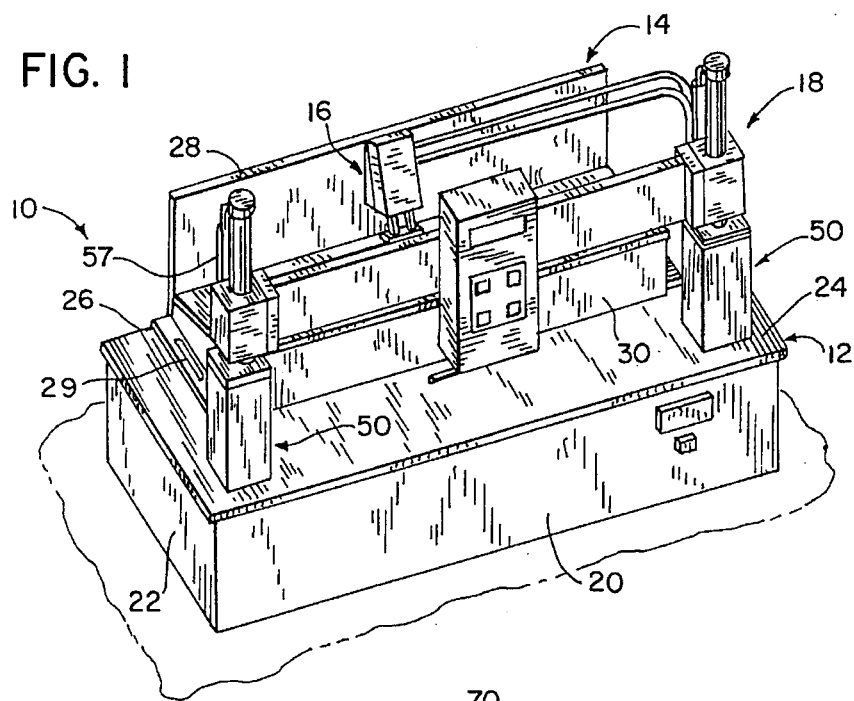
FIG. 1 is an isometric view of a score bend testing apparatus constructed according to the invention.
Figure 2:
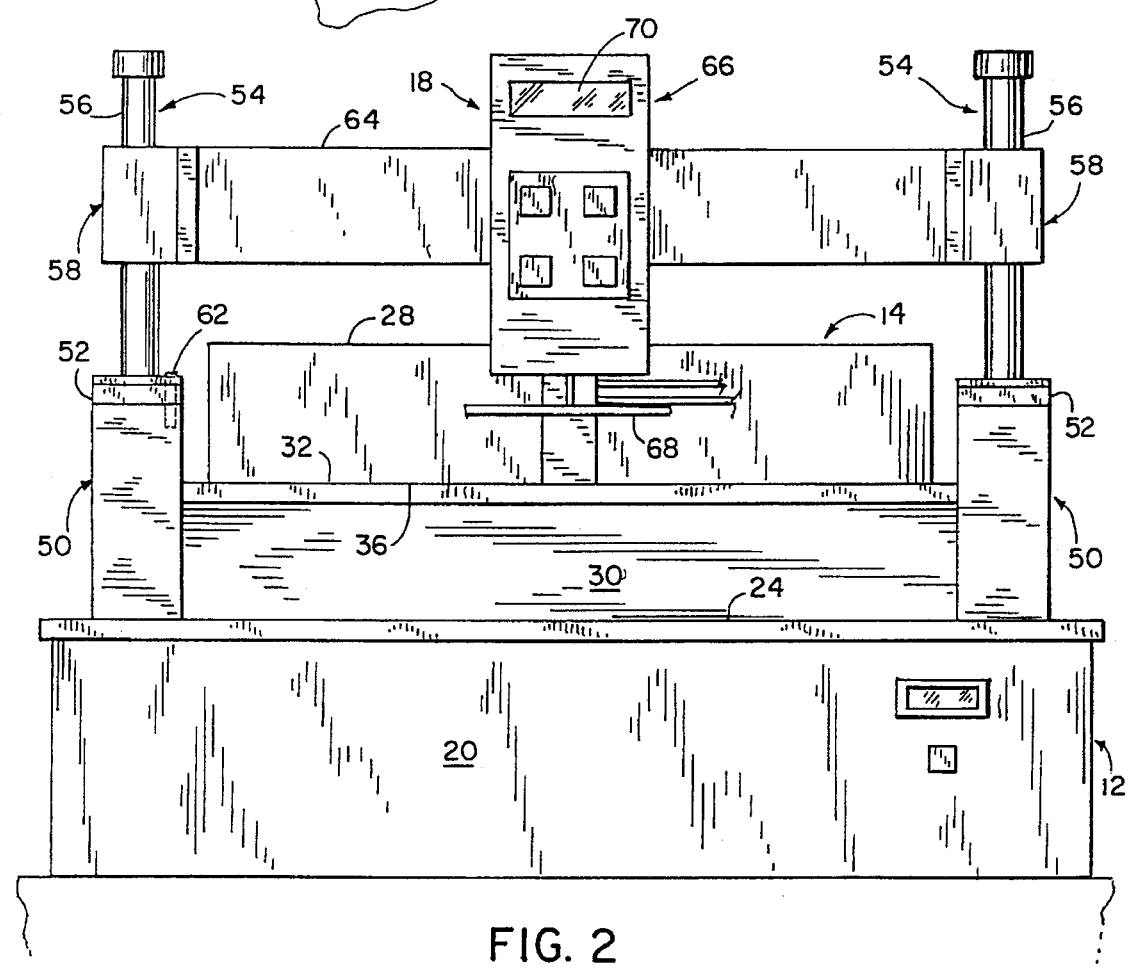
FIG. 2 is a front elevation view of the score bend testing apparatus of FIG. 1.
Figure 3:
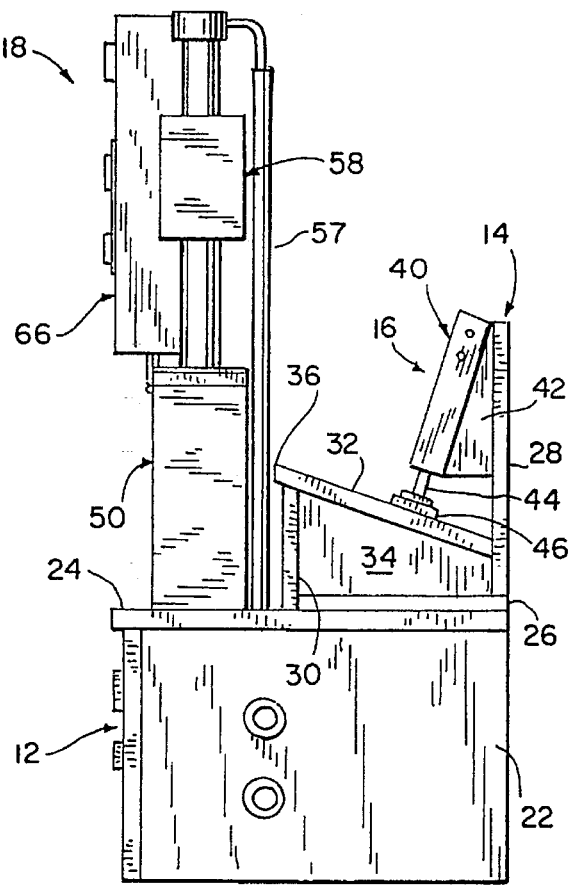
FIG. 3 is a side elevation view of the score bend testing apparatus of FIG. 1.

FIG. 1 illustrates a score bend testing apparatus 10 constructed according to the invention. Generally, apparatus 10 includes a box-like platform section 12, a base assembly 14, a clamping device 16, and a force-applying and measuring assembly 18.

Platform section 12 includes side walls 20, end walls 22 and an upper plate 24. Walls 20, 22 and plate 24 define an internal cavity within which the various electrical, pneumatic components associated with apparatus 10 are mounted. Base assembly 14 and force-applying and measuring assembly 18 are mounted to, and extend upwardly from, upper plate 24.

Base assembly 14 includes a lower, horizontal plate 26 which rests on platform upper plate 24, and a vertical rear plate 28 connected to and extending upwardly from the rear edge of lower plate 26. A pair of slots, one of which is shown at 29, are formed in the opposite ends of lower plate 26. Slots 29 each receive the shank of a bolt which extends into a threaded opening formed in lower plate 24, and provide back-and-forth adjustability in the position of base assembly 14 on upper plate 24. A vertical front plate 30 extends upwardly from upper plate 24 forwardly of the forward edge of lower plate 26. An angled support plate 32 is supported by the upper end of vertical front plate 30 and by a series of vertical filler plates 34. Filler plates 34 each define an angled upper edge engaging the lower surface of support plate 32 and, along with front plate 30, function to orient support plate 32 at an angle of approximately 15° relative to horizontal.

Rear plate 28 extends upwardly from the rear edge of support plate 32.

Support plate 32 defines an upper forward edge 36, defined by the apex of an acute angle between the upper surface of support plate 32 and its forward edge.

Clamping device 16 consists of a twin-rod air cylinder assembly 40 mounted to rear plate 28 via a triangular gusset plate 42. Cylinder assembly 40 includes a pair of extendible and retractable rods 44 having a clamping plate 46 connected to their outer ends, for selective movement toward and away from support plate 32 upon introduction of pressurized air to the opposite cylinder ends of air cylinder assembly 40, in accordance with conventional operation.

Force-applying and measuring assembly 18 includes a pair of pedestals 50 located one on either side of platform section 12. Pedestals 50 are mounted to and extend upwardly from the upper surface of upper plate 24, and each pedestal 50 has a vertical passage extending between its upper and lower ends. Each pedestal 50 includes an apertured double-layer upper cushion 52, and a rodless air cylinder assembly 54 extends through the vertical passage in each pedestal 50 and is mounted to upper plate 24. Each cylinder assembly 54 may be that such as is available from Bimba under its designation ULTRAN, Part No. US-049.25-CI-P. In accordance with conventional construction, each cylinder assembly 54 includes an output member which is movable relative to a cylinder body 56. A pair of vertical conduits 57 extend upwardly from upper plate 24, for routing pneumatic tubes to cylinder assemblies 54 from the interior of platform section 12.

A block 58 is mounted to the output member of each cylinder assembly 54, and is adapted for vertical up-and-down movement in response to conventional operation of each cylinder assembly 54.

Cushions 52 function to cushion the lower end of each block 58 during its downwardmost movement. A proximity switch 62 is mounted to the upper end of one of pedestals 50 and extends upwardly from the pedestal upper end. Proximity switch 62 is disposed within a recess formed in cushion 52, with the upper end of switch 62 being covered by the material of cushion 52 above the recess. Proximity switch 62 is interconnected with the actuation system for cylinder assemblies 54 to move blocks 58 upwardly after operation of cylinder assemblies 54 moves blocks 58 to their lowermost point.

A cross-member 64 extends between blocks 58. Cross-member 64 extends horizontally, and moves in a vertical up-down path upon synchronous operation of cylinder assemblies 54.

A force gauge assembly 66 is mounted to the central portion of cross-member 64. Force gauge assembly 66 includes a horizontal engagement rod 68 which extends parallel to support plate edge 36. Force gauge assembly 66 may be that such as is available from Chatilion under its Part No. OFS-10/SHAFT ONLY, and includes a visual readout screen 70 and conventional controls for calibration, resetting and the like.

Figure 6:
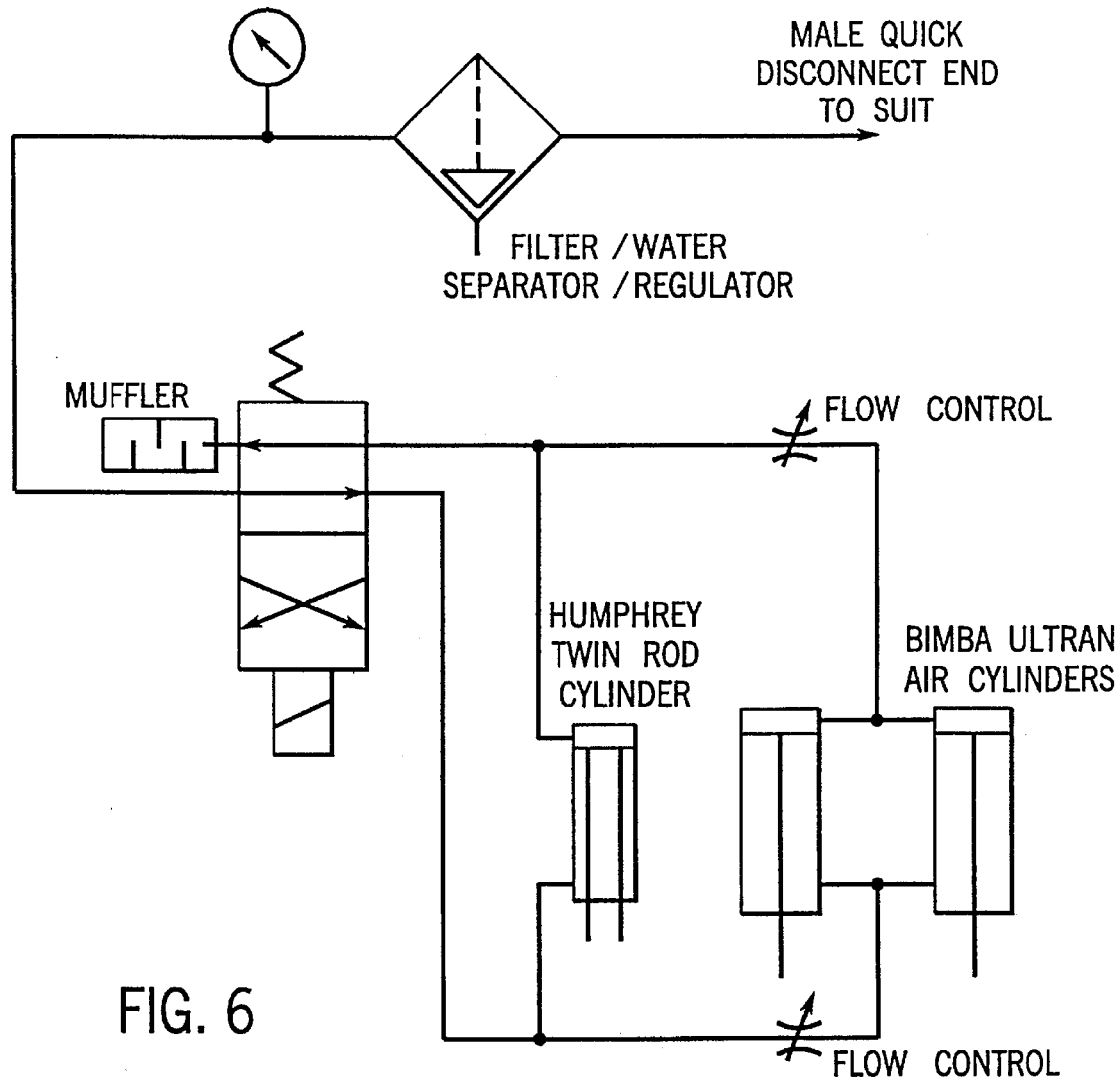
FIGS. 6 and 7 are schematic diagrams showing the pneumatic and electrical hydraulic systems for the score bend testing apparatus of FIG. 1.
Figure 7:
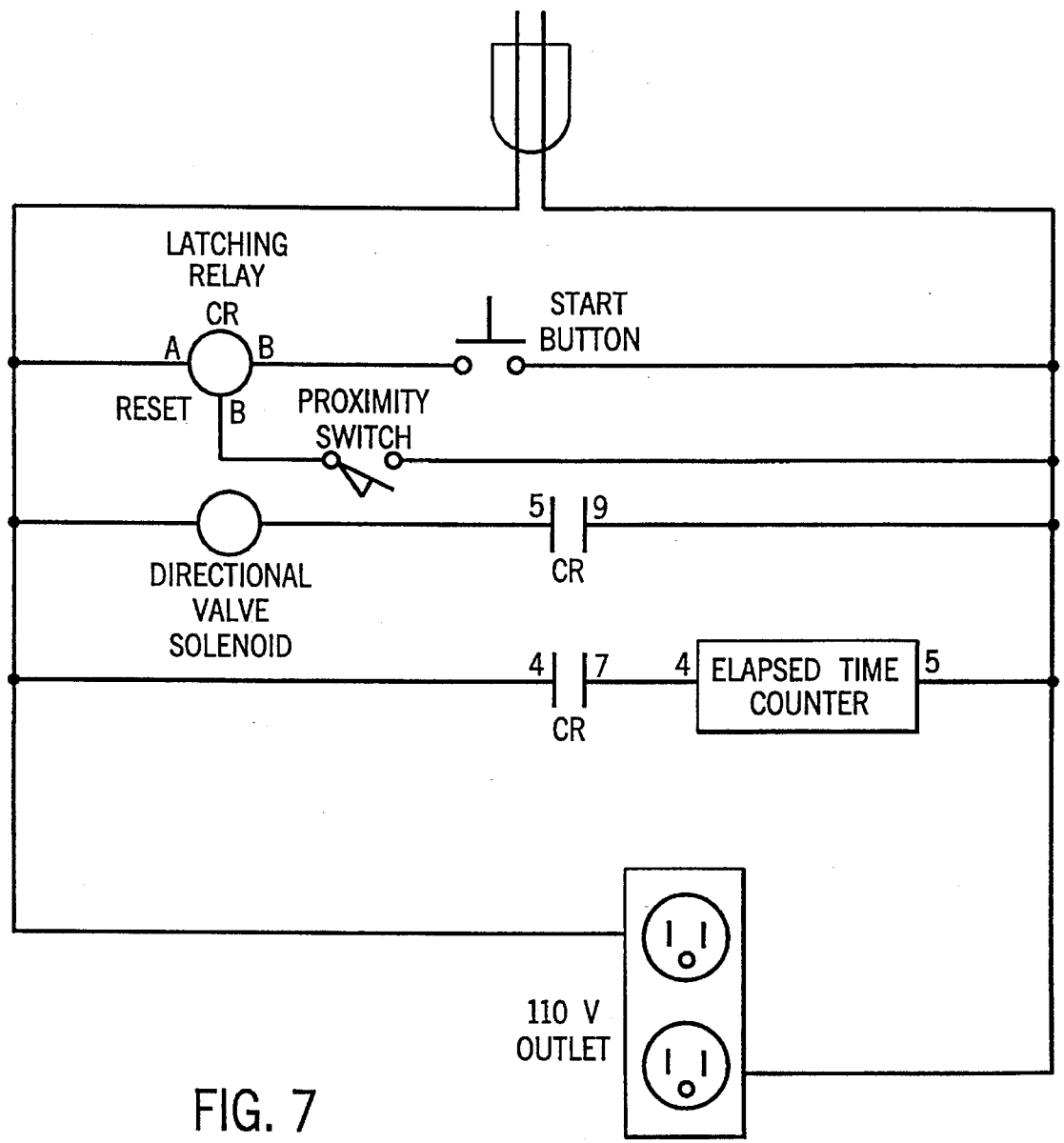

FIG. 6 illustrates the pneumatic circuit used to operate apparatus 10, and FIG. 7 shows the electrical system for apparatus 10. These systems are mounted within the interior of platform assembly 12, and illustrate an embodiment of apparatus 10 which has been found to be satisfactory in construction and operation. It is understood that other satisfactory control and operational systems could be employed.

Figure 4:
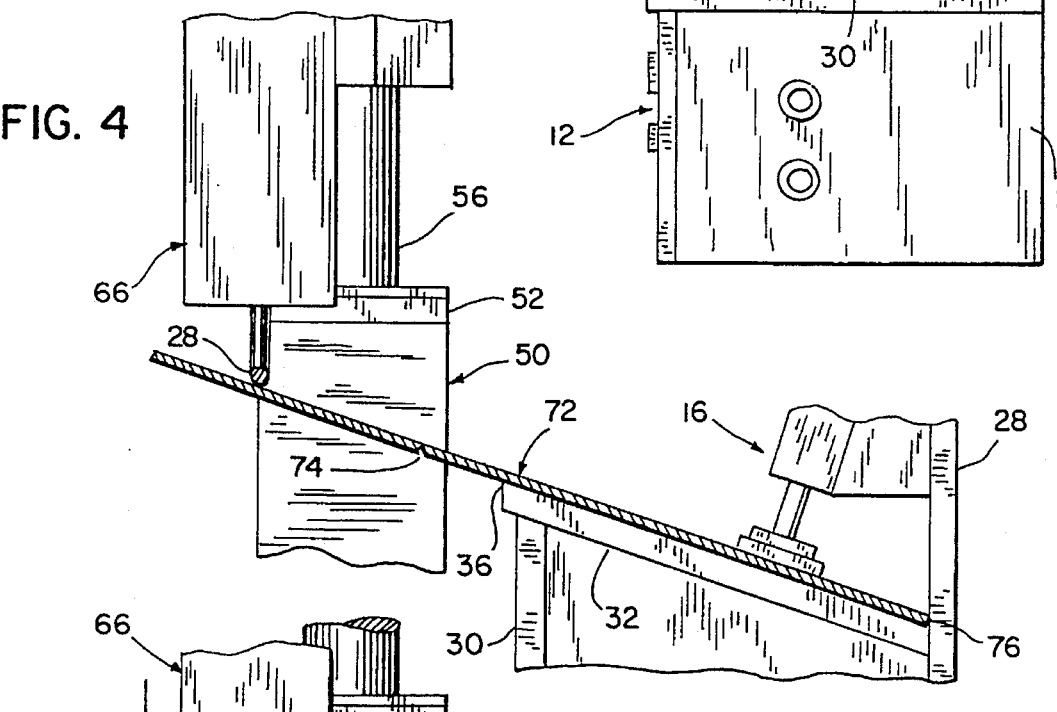
FIGS. 4 and 5 are partial elevation views, with portions in section, showing operation of the score bend testing apparatus of FIG. 1.
Figure 5:
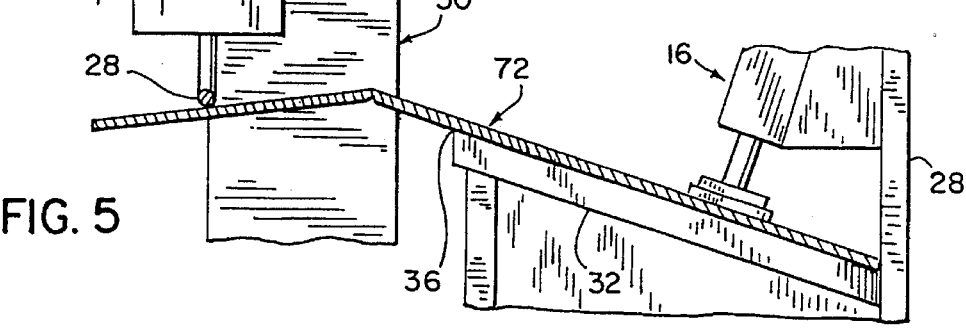

In operation, apparatus 10 functions as follows. The operator first cuts a section or sheet of corrugated board, such as shown in FIGS. 4 and 5 at 72, and places sheet 72 on support plate 32 between pedestals 50 such that a score 74 therewithin is located at a predetermined spacing relative to a rear edge 76 of board 72 and thereby relative to support plate forward edge 36. The operator then places sheet 72 such that rear edge 76 of sheet 72 engages the forward surface of upstanding rear plate 28 to locate score 74 a predetermined spacing forwardly of edge 36, as shown in FIGS. 4 and 5. The position of base assembly 24 can be adjusted to vary the spacing between score 74 and engagement rod 68. The operator then initiates operation by engaging a switch which results in actuation of clamping device 16 and extension of its rods 44 to engage clamping plate 46 with sheet 72, to clamp sheet 72 against the upper surface of support plate 32. The operation of apparatus 10 is sequential, and then commences operation of cylinder assemblies 54 so as to initiate downward movement of blocks 58 and cross-member 64, which results in downward movement of force gauge assembly 66 and engagement rod 68. Engagement rod 68 then engages the upwardly facing surface of sheet 72 forwardly of score 74, and operation of cylinder assemblies 54 continues until sheet 72 is bent about score 74, as shown in FIG. 5. This provides approximately a 30° bend of sheet 72 at score 74. Force gauge assembly 66 then provides a readout on screen 70 as to the maximum amount of force transferred thereto through engagement rod 68, to provide a visual readout to the operator as to the amount of force required to bend sheet 72 at score 74. When blocks 58 attain their lowermost position, proximity switch 62 functions to reverse operation of cylinder assemblies 54 to return blocks 58 to their upwardmost position prior to commencement of another cycle.

It can thus be appreciated that apparatus 10 applies a force to sheet 72 which is not operator-dependent. That is, the pneumatic actuation and downward movement of force gauge assembly 66 is carried out independent of the operator after the operator has initiated the sequential and automatic operation of apparatus 10. This provides a highly consistent and reliable application of force during downward movement of cross-member 64, which in turn provides accurate and consistent readings of the amount of force required to bend sheet 72 at score 74.

As can be seen in FIG. 7, the control system utilized in apparatus 10 includes an elapsed time counter, which functions to maintain apparatus 10 in calibration. The elapsed time counter functions to determine, for each cycle, the amount of time elapsed from the beginning of the cycle until proximity switch 62 is actuated. In response to the cycle time, the flow control valve in the pneumatic system of apparatus 10, as shown in FIG. 6, is adjusted to ensure that cycle time is maintained consistent, which in turn corresponds to consistency in the amount of force applied by engagement member 68 by pneumatic operation of cylinder assemblies 54.

Various alternatives and embodiments are contemplated as being within the scope of the following claims particularly pointing out and distinctly claiming the subject matter regarded as the invention.

I claim:

1. A score bend testing apparatus used by an operator for testing the amount of force required to bend a sheet of material at a longitudinal score, comprising:

a base having a planar support surface and defining an edge;

a clamp for clamping the sheet of material against the support surface such that the score is located outwardly of the edge;

an operator-independent force applying arrangement responsive to the clamping of the sheet of material for automatically applying a concentrated force to the sheet of material outwardly of the score and for continuing application of the force until the sheet bends at the score; and an operator-independent force measuring arrangement interconnected with the force applying arrangement for automatically determining the actual amount of force applied to bend the sheet at the score.

2. A score bend testing apparatus for testing the amount of force required to bend a sheet of material at a longitudinal score, comprising:

a base having an upwardly facing planar support surface and defining an edge, wherein the upwardly facing planar support surface is oriented at an angle to horizontal such that the edge is associated with a forward portion of the support surface which is elevated relative to a rearward portion of the support surface;

a clamp for clamping the sheet of material against the support surface such that the score is located outwardly of the edge;

a force applying arrangement for applying a downward force to the sheet of material outwardly of the score and for continuing application of the downward force until the sheet bends at the score; and a force measuring arrangement interconnected with the force applying arrangement for determining the amount of force applied to bend the sheet at the score.

3. The apparatus of claim 2, wherein the base includes an upstanding member associated with its rear portion for engaging a rear edge defined by the sheet of material for positioning the sheet of material relative to the forward edge of the base.

4. The apparatus of claim 3, wherein the clamp is mounted to the upstanding member.

5. A score bend testing apparatus for testing the amount of force required to bend a sheet of material at a longitudinal score, comprising:

a base having a planar support surface and defining an edge;

a clamp for clamping the sheet of material against the support surface such that the score is located outwardly of the edge;

a force applying arrangement for applying a transverse force to the sheet of material outwardly of the score and for continuing application of the force until the sheet bends at the score, wherein the force applying arrangement includes a pair of spaced supports; an operating device mounted to each support for selective reciprocating movement in a first direction toward the sheet of material and in a second direction away from the sheet of material; a cross-member extending between and interconnected with each operating device for selective movement therewith in the first and second directions; and an engagement member mounted to the cross-member for engaging the sheet of material upon movement of the cross-member in the first direction; and a force measuring arrangement interconnected with the force applying arrangement for determining the amount of force applied to bend the sheet at the score.

6. The apparatus of claim 5, wherein each operating device comprises a cylinder assembly having an upwardly and downwardly movable output member.

7. The apparatus of claim 5, wherein the cross-member comprises an axial member spanning between the operating devices and located outwardly of the edge of the base.

8. The apparatus of claim 5, wherein the force measuring arrangement is mounted to the cross-member along with the force applying arrangement.

9. The apparatus of claim 8, wherein the force measuring arrangement comprises a force measuring unit, with which the engagement member is associated, mounted to the cross-member.

10. A score bend testing apparatus for testing the amount of force required to bend a sheet of material at a longitudinal score, comprising:

a base having a planar support surface and defining an edge;

a clamp for clamping the sheet of material against the support surface such that the score is located outwardly of the edge;

a force applying arrangement for applying a transverse force to the sheet of material outwardly of the score and for continuing application of the force until the sheet bends at the score, wherein the force applying arrangement comprises a rod engageable with the sheet of material for applying the transverse force thereto, wherein the rod is spaced a predetermined substantially constant distance from the score when the rod is in contact with the sheet of material, such that the transverse force is applied to the sheet of material along an axis parallel to the score; and a force measuring arrangement interconnected with the force applying arrangement for determining the amount of force applied to bend the sheet at the score.

11. The apparatus of claim 10, wherein the rod, the score and the forward edge of the base are oriented parallel to each other.

12. A score bend testing apparatus for testing the amount of force required to bend a sheet of material at a longitudinal score, comprising:

a base having an upwardly facing planar support surface, wherein the support surface defines a forward edge and is arranged so as to extend in a downward direction rearwardly of the forward edge;

a clamp for clamping the sheet of material against the support surface, wherein the sheet of material is placed on the base such that the score is located outwardly of the forward edge of the support surface; and a force applying and measuring arrangement, comprising a pair of supports; an operating device mounted to each support for selective upward and downward movement; a cross-member extending between and interconnected with the operating devices for selective upward and downward movement therewith; an engagement member in the form of a rod extending along an axis parallel to the score; wherein the supports and cross-member are arranged such that the engagement member is located forwardly of the score; and a force measuring device interconnected with the engagement member for measuring the amount of force required to bend the sheet of material at the score during downward movement of the engagement member and the cross-member through the operating devices.

13. A method of determining the amount of force required to bend a sheet of material at a longitudinal score, comprising the steps of:

clamping the sheet of material against a support surface such that the score is located outwardly of a forward edge defined by the support surface;

applying a transverse force to the sheet of material outwardly of the score, wherein the step of applying a transverse force to the sheet of material is carried out by operating a pair of spaced, movable members so as to impart movement to a cross-member extending between and interconnected with the movable members in a direction toward the sheet of material and substantially perpendicular to the plane defined by the sheet of material;

continuing application of the transverse force until the sheet of material bends at the score; and measuring the amount of force required to bend the sheet of material at the score.

14. The method of claim 13, wherein the step of clamping the sheet of material is carried out after positioning the sheet of material such that a rearward edge defined by the sheet of material engages a support edge associated with the rearward portion of the support surface.

15. A score bend testing apparatus for testing the amount of force required to bend a sheet of material at a longitudinal score, comprising:

a base having an upwardly facing planar support surface and defining an edge;

a clamp for clamping the sheet of material against the support surface such that the score is located outwardly of the edge;

a force applying arrangement for applying a downward force to the sheet of material outwardly of the score and for continuing application of the downward force until the sheet bends at the score; and a force measuring arrangement interconnected with the force applying arrangement for determining the amount of force applied to bend the sheet at the score;

wherein the upwardly facing planar support surface is oriented at an angle to horizontal such that the edge is associated with a forward portion of the support surface which is elevated relative to a rearward portion of the support surface; and wherein the base includes an upstanding member associated with its rear portion for engaging a rear edge defined by the sheet of material for positioning the sheet of material relative to the forward edge of the base.

16. The method of claim 13, wherein the step of measuring the amount of force required to bend the sheet at the score is carried out by mounting a force applying and measuring unit to the cross-member which functions to apply the force to the sheet of material via an engagement member and to measure the amount of force applied to the sheet of material by the engagement member.

17. The method of claim 16, wherein the step of applying the downward force to the sheet of material is carried out through an elongated engagement member in the form of a rod extending along an axis substantially parallel to the axis of the score.

* * * * *